(12) United States Patent
Jia et al.

(10) Patent No.: US 11,874,426 B2
(45) Date of Patent: Jan. 16, 2024

(54) EXPERIMENTAL APPARATUS AND EXPERIMENTAL METHOD FOR PHYSICAL MODELING OF FLUID MIGRATION AND ACCUMULATION PROCESS WITH CONTEMPORANEOUS STRUCTURAL DEFORMATION

(71) Applicant: NANJING UNIVERSITY, Nanjing (CN)

(72) Inventors: Dong Jia, Nanjing (CN); Xiaojun Wu, Nanjing (CN); Zhuxin Chen, Nanjing (CN); Shufeng Yang, Nanjing (CN); Hanlin Chen, Nanjing (CN); Jianying Yuan, Nanjing (CN); Hongwei Yin, Nanjing (CN); Yiquan Li, Nanjing (CN); Guoai Xie, Nanjing (CN); Yinqi Li, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 563 days.

(21) Appl. No.: 17/201,006

(22) Filed: Mar. 15, 2021

(65) Prior Publication Data
US 2021/0199847 A1    Jul. 1, 2021

(30) Foreign Application Priority Data

Jan. 20, 2021   (CN) .......................... 202110076851.4

(51) Int. Cl.
*G01V 99/00*    (2009.01)
*B04B 5/10*    (2006.01)

(52) U.S. Cl.
CPC .............. *G01V 99/005* (2013.01); *B04B 5/10* (2013.01); *G01V 2210/645* (2013.01)

(58) Field of Classification Search
CPC ............ G01V 99/005; G01V 2210/645; B04B 5/10
See application file for complete search history.

(56) References Cited

FOREIGN PATENT DOCUMENTS

| CN | 2857006 Y | * | 1/2007 | ............. G01N 33/00 |
|---|---|---|---|---|
| CN | 109166441 A | * | 1/2019 | ............. G09B 23/40 |
| CN | 109493705 A | * | 3/2019 | ............. G09B 23/40 |
| CN | 106841028 B | * | 7/2023 | ............. G01N 19/00 |

OTHER PUBLICATIONS

Hou YJ. Development of geotechnical centrifuges and facilities in China. InPhysical Modelling in Geotechnics, vol. 1 Jul. 11, 2018 (pp. 77-85). CRC Press. (Year: 2018).*

* cited by examiner

*Primary Examiner* — Chuen-Meei Gan
(74) *Attorney, Agent, or Firm* — CBM PATENT CONSULTING, LLC

(57) ABSTRACT

It discloses an experimental apparatus and experimental method for physical modeling of a fluid migration and accumulation process with contemporaneous structural deformation. The experimental apparatus comprises a structural deformation experiment box, a structural deformation control device, a fluid control device and an experimental control device; the structural deformation experiment box is installed in a basket experiment module on a cantilever of a drum centrifuge, the structural deformation control device can extend and compress an experimental model in horizontal and vertical directions; and fluid cylinders of the fluid control device can be filled with fluids or plastic materials.

7 Claims, 3 Drawing Sheets

EXPERIMENTAL APPARATUS AND EXPERIMENTAL METHOD FOR PHYSICAL MODELING OF FLUID MIGRATION AND ACCUMULATION PROCESS WITH CONTEMPORANEOUS STRUCTURAL DEFORMATION

This application claims priority to Chinese Patent Application Ser. No. CN202110076851.4 filed on 20 Jan. 2021.

TECHNICAL FIELD

The present invention relates to an experimental apparatus and experimental method for physical modeling, in particular to an experimental apparatus and an experimental method for a physical modeling experiment of a fluid migration and accumulation process with contemporaneous structural deformation.

BACKGROUND

Physical modeling for structural deformation is a method capable of modeling and studying large-scale structural deformation under laboratory conditions, and have wide applicability. Physical modeling experiments in a hypergravity environment created by centrifuges have made great progress in the middle of last century. In recent decades, scholars have made great progress in the research fields of lithospheric rift extension, mid-ocean ridge spreading mechanism, fold-and-thrust structure, strike-slip pull-apart structure, gypsum-salt and magma diapir structure through hypergravity structural physical modeling experiments using centrifuges.

Hypergravity structural physical modeling experiments based on large long-arm centrifuges can highlight the flow effects of lithosphere under relatively uniform hypergravity conditions, effectively solve the common problem of interference of various factors under normal gravity conditions, and provide an effective research tool for modeling a geologic structural process involving rock rheology, such as mantle plume upwelling, asthenosphere convection, lower crustal flow, magmatic intrusion, and flow of weak strata such as gypsum-salt and shale in upper crust. However, due to complex structures of large long-arm centrifuges, and high manufacturing and operation costs, most scholars use drum centrifuges with lower cost and smaller size to carry out structural physical modeling experiments in the hypergravity environment. The turntable rotating structure of small drum centrifuges restricts experimental materials to viscous materials, so that loose experimental materials cannot be used, and experiments on interaction between brittle deformation and plastic deformation cannot be carried out. Meanwhile, both long-arm centrifuges and drum centrifuges cannot accurately control the deformation of experimental materials in environment larger than 300 g, the effect of modeling structural deformation is limited, and there is a certain gap with the real environment.

SUMMARY

Purpose of the present invention: the purpose of the present invention is to provide an experimental apparatus for a multiphase fluid migration and accumulation process with contemporaneous structural deformation capable of accurately controlling the structural deformation and fluid injection rate in a 2500 g hypergravity environment.

Technical solution: an experimental apparatus for physical modeling of a multiphase fluid migration and accumulation process with contemporaneous structural deformation based on a hanging drum centrifuge, comprising a structural deformation experiment box, a structural deformation control device for accurately controlling the structural deformation rate and a fluid control device for accurately controlling the fluid injection rate; the structural deformation experiment box is installed inside a basket experiment module on a cantilever of a drum centrifuge; and the fluid control device comprises fluid cylinders filled with fluids or plastic materials.

The experimental apparatus of the present invention further comprises an experimental control device arranged outside the centrifuge, comprising a console, a control cabinet, a hydraulic control station, a flowmeter and a pressure gauge; a liquid slip ring is arranged on a rotating shaft of the centrifuge, and a hydraulic pipeline for connecting the experimental control device and the hydraulic cylinder is arranged on a rotating arm of the centrifuge.

The fluid control device further comprises a fluid injection lifting device and an injection pipe; the fluid cylinders are connected with an injection port on a frame of the structural deformation experiment box through the injection pipe; the fluid cylinders are further provided with a feeding port and a pressure column; and the top of the pressure column is connected with the fluid injection lifting device.

The structural deformation control device comprises a lifting device, a lifting slide rail, a translation connecting plate, a translation slide rail and a triangular push plate; the lifting slider on the lifting device drives the triangular push plate to extend and compress an experimental model in the vertical direction; and the translation slider on the translation connecting plate drives the triangular push plate to extend and compress the experimental model in the horizontal direction.

The fluid injection lifting device is connected with a first hydraulic cylinder, and the lifting device is connected with a second hydraulic cylinder.

The structural deformation experiment box comprises a frame, a base plate and a model support base plate; a transparent window is arranged on the frame; and experimental materials are placed in the frame.

The experimental method of the present invention comprises the following steps: (a) spreading experimental materials in the structural deformation experiment box, and filling the injection pipe with fluids or plastic materials; (b) placing a structural deformation experiment box in one basket experiment module; placing a counterweight with the same weight as the structural deformation experiment box in the other basket experiment module, and sealing relevant pipelines; (c) turning on the centrifuge to allow the running acceleration to reach a set value; and setting the flow rate, flow and pressure of the fluids or the plastic materials on the console; and (d) stopping relevant equipment, disconnecting the pipelines and taking out the structural deformation experiment box.

The step of filling the injection pipe with fluids or plastic materials in the step (a) specifically comprises: injecting the fluids or the plastic materials into the fluid cylinders through a feeding port until fluids or plastic materials overflow from an air vent on the fluid cylinders; opening the injection port, and controlling the fluid injection lifting device to descend slowly through the console until fluids or plastic materials overflow from the injection port.

In the step (c), the plastic materials are injected when the set injection rate is positive, and the plastic materials are suctioned when the injection rate is negative.

Advantageous effects: (1) the experimental apparatus is based on a small hanging drum centrifuge, which saves the manufacturing and operation costs; (2) a physical modeling experiment for a multiphase fluid migration and accumulation process with contemporaneous structural deformation is realized in a 2500 g hypergravity environment; (3) the structural deformation rate of the experimental materials can be accurately controlled; (4) the fluid injection time and rate can be controlled, the laws of fluid migration and accumulation during or after structural deformation can be studied, with the minimum fluid injection rate of 0.1 ml/min; and (5) plastic materials can be injected into an experimental model for structural deformation at a minimum injection rate of 1 ml/min.

DETAILED DESCRIPTION

The technical solutions of the present invention will be further described with reference to the accompanying drawings.

The experimental apparatus of the present invention is suitable for a physical modeling experiment for a multiphase fluid migration and accumulation process with lithospheric contemporaneous structural deformation in a 10-2500 g centrifugal hypergravity environment, and particularly suitable for a physical modeling experiment for a multiphase fluid migration and accumulation process with lithospheric contemporaneous structural deformation in a 200-2500 g centrifugal hypergravity environment.

The experimental apparatus of the present invention comprises a drum centrifuge, a structural deformation experiment box, an experimental control device, a structural deformation control device and a fluid control device.

Figure 1:
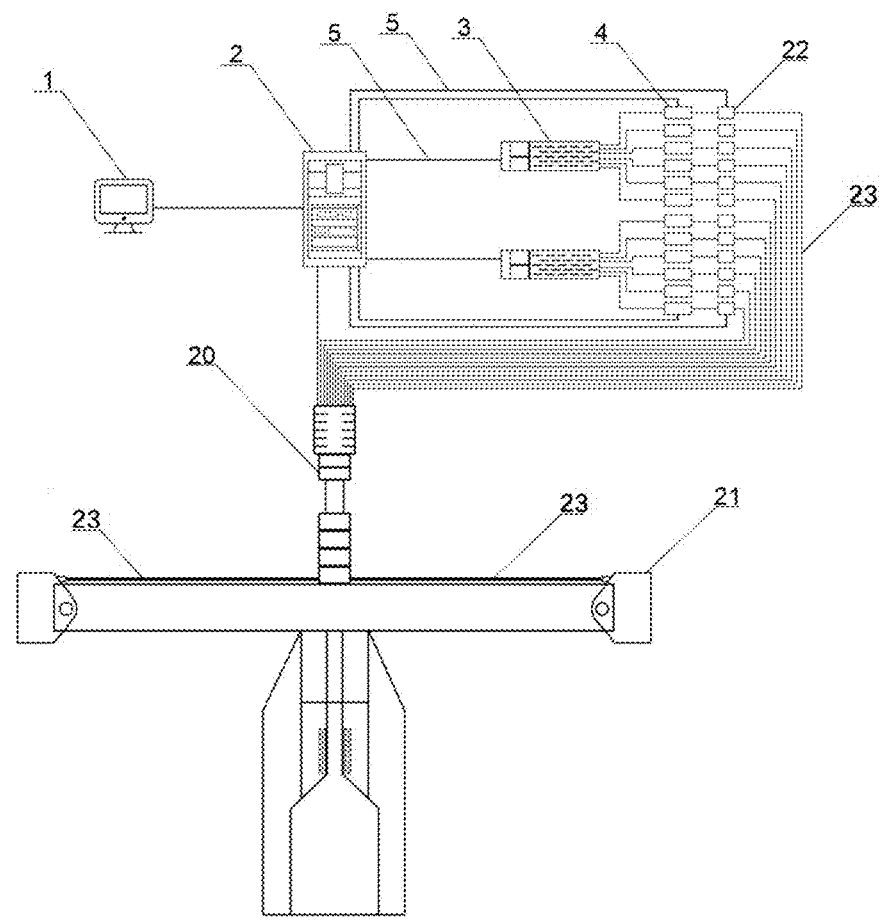
FIG. 1 is a structural diagram of the experimental apparatus of the present invention.
Figure 2:
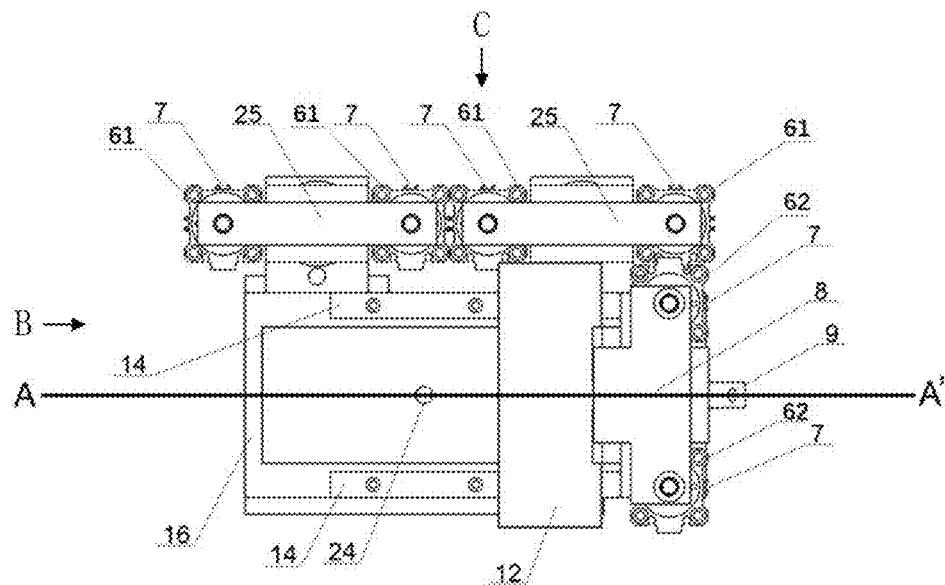
FIG. 2 is a top view of the experiment box of the present invention.
Figure 3:
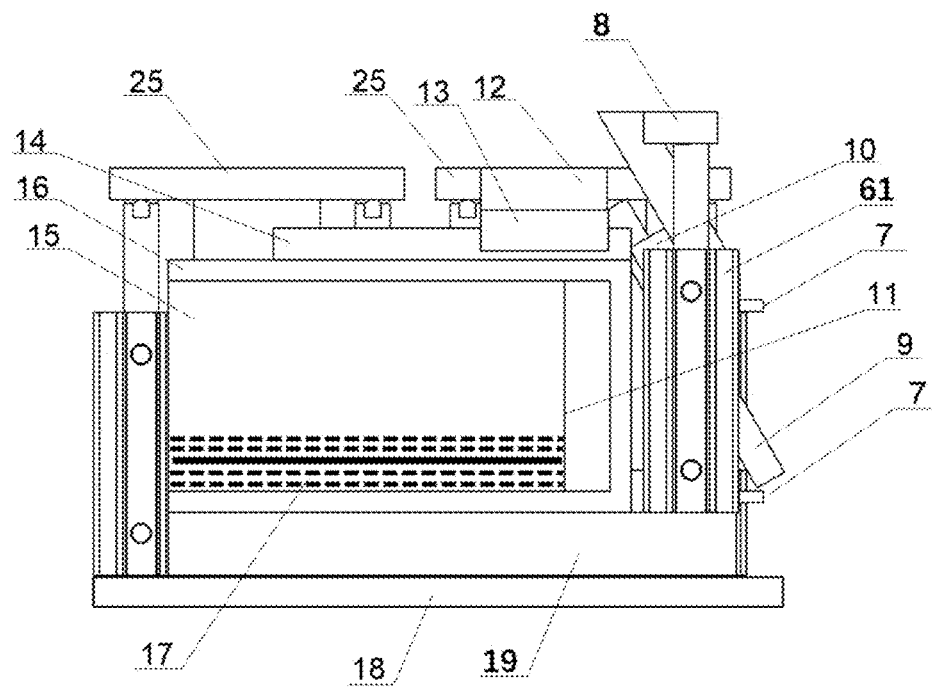
FIG. 3 is a side view of the experiment box of the present invention in a B direction.
Figure 4:
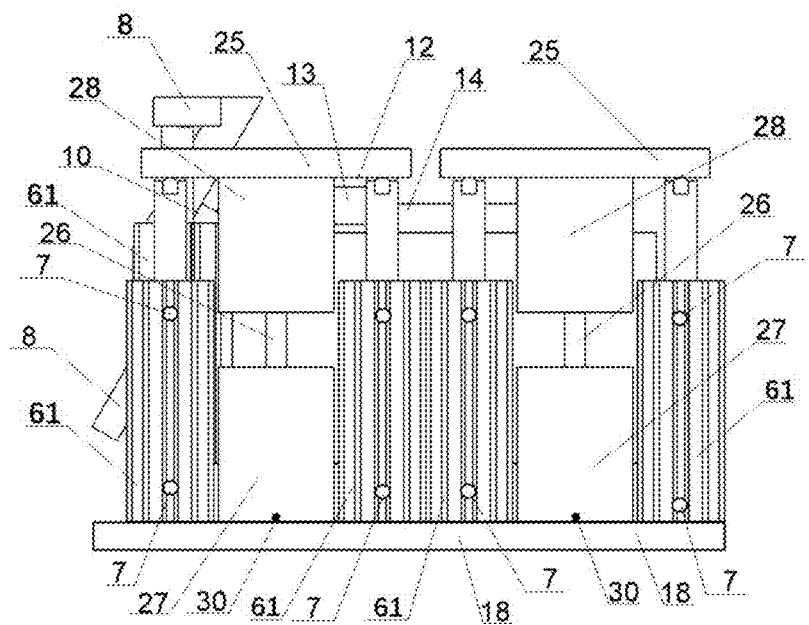
FIG. 4 is a side view of the experiment box of the present invention in a C direction.
Figure 5:
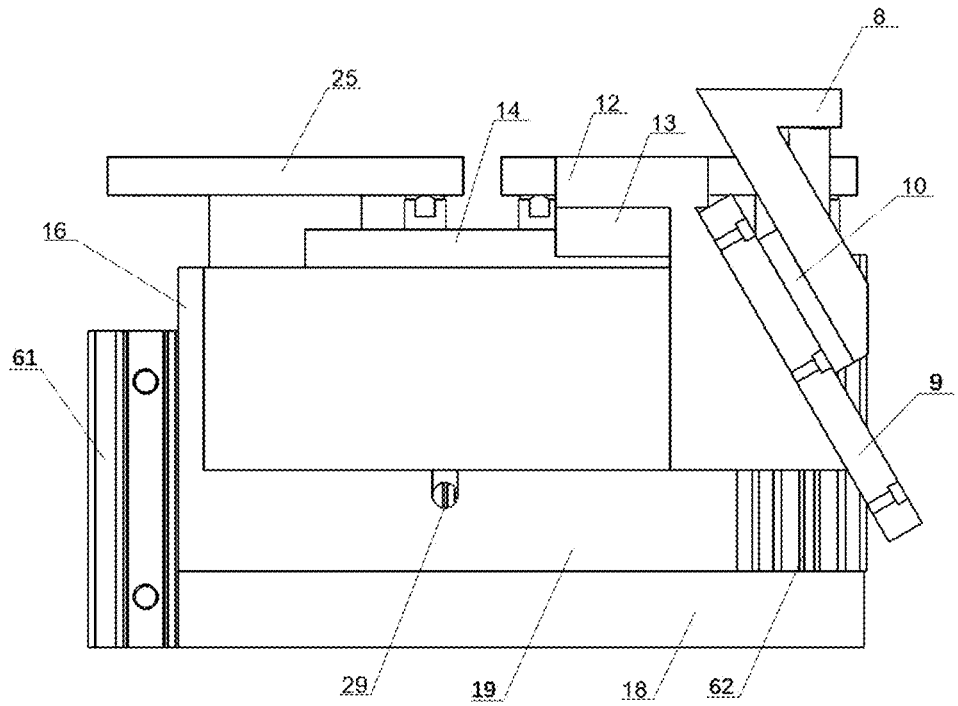
FIG. 5 is an A-A' sectional view of the experiment box of the present invention.

As shown in FIG. 1, the structural deformation experiment box of the experimental apparatus is installed in a basket experiment module 21 on a cantilever of the drum centrifuge, and the experimental control device is arranged outside the centrifuge; the experimental control device comprises a console 1, a control cabinet 2, a hydraulic control station 3, a flowmeter 4 and a pressure gauge 22; the control cabinet 2 is connected with the hydraulic control station 3, the flowmeter 4 and the pressure gauge 22 through control lines 5; a hydraulic pipeline 23 is arranged on a rotating arm of the centrifuge, a liquid slip ring 20 is arranged on a rotating shaft of the centrifuge, and a hydraulic cylinder inside the experiment box is connected with the pressure gauge 22 and the flowmeter 4 through the hydraulic pipeline 23.

As shown in FIG. 2 to FIG. 5, the structural deformation experiment box comprises a frame 16, a base plate 18 and a model support base plate 19; experimental materials 17 are placed in the frame 16; the experimental materials can be selected from brittle materials and plastic materials, and the centrifugal force at the bottom of the basket experiment module 21 is up to 2500 g during the experiment. A transparent window 15 is arranged on the frame 16 for observing a structural deformation process and a fluid migration and accumulation process of the experimental materials.

The structural deformation control device comprises a lifting device 8, a lifting slide rail 9, a lifting slider 10, a translation connecting plate 12, a translation slider 13, a translation slide rail 14 and a triangular push plate 11; the lifting slider 10 on the lifting device 8 is connected with the triangular push plate 11, and the lifting slider 10 slides up and down along the lifting slide rail 9 to drive the triangular push plate 11 to compress and extend an experimental model; the translation connecting plate 12 is connected with the lifting device 8, and the translation slider 13 on the translation connecting plate 12 is connected with the triangular push plate 11, and the translation slider 12 moves side to side along the translation slide rail 14 to drive the triangular push plate 11 to compress and extend the experimental model. A second hydraulic cylinder 62 is connected with the lifting device 8 for providing driving power for structural deformation; a hydraulic interface 7 on the second hydraulic cylinder 62 is connected with the experimental control device through the hydraulic pipeline 23, the experimental control device accurately controls the motion rate of the lifting device 8, and the minimum structural deformation rate is 0.01 mm/s.

The fluid control device comprises a first hydraulic cylinder 61 and fluid cylinders 27; a hydraulic interface 7 on the first hydraulic cylinder 61 is connected with the hydraulic control station 3 through the hydraulic pipeline 23; the fluid cylinders 27 are provided with a feeding port 30 for feeding fluid into the fluid cylinders 27; the experiment box is provided with an injection port 24 for injecting fluids into the experimental materials, and the fluid cylinders 27 are connected with the injection port 24 through an injection pipe 29; the fluid cylinders 27 are provided with a pressure column 26, the top of the pressure column 26 is connected with a fluid injection lifting device 25, the first hydraulic cylinder 61 controls the fluid injection lifting device 25 to drive the pressure column 26 to move, and the pressure column 26 drives a piston in the fluid cylinders 27 to compress the fluids down, injecting the fluids into the experimental model through the injection pipe 29 and the injection port 24.

The two fluid cylinders 27 can be filled with different fluids, such as purified water, white oil and kerosene, and the fluids can be injected into the experimental model during or after structural deformation to study the fluid migration and accumulation laws with contemporaneous structural deformation and the fluid migration and accumulation laws after structural formation. The hydraulic control station 3 accurately controls the fluid filling rate, and the minimum fluid injection rate is 0.1 ml/min. The fluid cylinders 27 can also be filled with plastic materials such as silica gel and vaseline to model the influence of magmatism or diapirism on structural deformation during contemporaneous structural deformation, and the hydraulic control station 3 controls the minimum plastic material injection or suction rate at 1 ml/min.

An experiment using the experimental apparatus of the present invention comprises the following processes:

(1) Preparation for experiment:

(11) experiment box: connecting the hydraulic interface 7 of the first hydraulic cylinder 61 with the hydraulic control station 3, and controlling the fluid injection lifting device 25 to ascend through the console 1, with the ascending height less than or equal to the thickness of the model support base plate 19; sealing the injection port 24, opening an air vent on a plunger cover of the fluid cylinders 27, injecting fluids into the fluid cylinders 27 through the feeding port 30 until the fluids overflow from the air vent, screwing the sealing screw of the air vent tightly, and then screwing the sealing screw of the feeding port 30 tightly; opening the injection port 24, controlling the fluid injection lifting device 25 to descend slowly through the console 1 until the fluids overflow from the injection port 24 to ensure that the fluid injection pipe 29 is filled with the fluids, and cleaning up the fluids overflowing from the injection port 24; spreading the experimental materials 17 in the structural deformation experiment box, and disconnecting the hydraulic interface 7 of the first hydraulic cylinder 61 from the hydraulic control station 3.

(12) counterweight and pipeline: installing the experiment box in one basket experiment module 21, connecting the hydraulic pipeline 23 with the liquid slip ring 20, and connecting the hydraulic pipeline 23 with the hydraulic interfaces 7 of the first hydraulic cylinder 61 and the second hydraulic cylinder 62 in the experiment box; installing a counterweight with the same weight as the experiment box in the other basket experiment module 21, sealing the hydraulic pipeline 23; and closing the centrifuge cover.

(2) Structural deformation: turning on the centrifuge to allow the running acceleration of the centrifuge to reach a set value, and setting parameters for compressing or extending the experimental model by the second hydraulic cylinder 62 on the console 1, including motion distance, motion time and motion rate, for compressional deformation when the motion distance is positive, and extensional deformation when the motion distance is negative; and detecting parameters such as hydraulic flow rate, flow and pressure of the second hydraulic cylinder 62 in the structural deformation control device in real time by the console 1.

(3) Fluid injection: calculating parameters such as hydraulic flow rate, flow and pressure of the fluid control device based on preset parameters such as fluid injection rate, flow and time by the console 1, and controlling the hydraulic control station 3 by the console 1 to lower the first hydraulic cylinder 61, thus lowering the fluid injection lifting device 25 to drive the pressure column 26 and the piston in the fluid cylinders 27 to compress the fluids into the experimental model.

(4) Plastic material injection or suction: injecting plastic materials into the fluid cylinders 27, and calculating parameters such as hydraulic flow rate, flow and pressure based on preset parameters by the console 1; injecting the plastic materials when the injection rate is positive, and suctioning the plastic materials when the injection rate is negative.

(5) End of experiment: stopping injecting and suctioning the fluids and the plastic materials, stopping the centrifuge, disconnecting relevant pipelines, and taking out the structural deformation experiment box to complete the experiment.

What is claimed is:

1. An experimental apparatus for physical modeling of a fluid migration and accumulation process with contemporaneous structural deformation, comprising a structural deformation experiment box, a structural deformation control device and a fluid control device; wherein the structural deformation experiment box is installed in a basket experiment module (21) on a cantilever of a drum centrifuge; the structural deformation control device comprises a hydraulically driven triangular push plate (11) moving in vertical and horizontal directions; and the fluid control device comprises fluid cylinders (27) filled with fluids or plastic materials;

wherein the fluid control device further comprises a fluid injection lifting device (25), a pressure column (26) and an injection pipe (29); the fluid cylinders (27) are connected with an injection port (24) on a frame (16) of the structural deformation experiment box through the injection pipe (29).

2. The experimental apparatus for physical modeling of a fluid migration and accumulation process with contemporaneous structural deformation according to claim 1, further comprising an experimental control device, wherein the experimental control device comprises a hydraulic control station (3) for controlling injection of fluid and liquid in a hydraulic cylinder, a flowmeter (4) and a pressure gauge (22); a liquid slip ring (20) is arranged on a rotating shaft of the centrifuge, and a hydraulic pipeline (23) for connecting the experimental control device and the hydraulic cylinder is arranged on a rotating arm of the centrifuge.

3. The experimental apparatus for physical modeling of a fluid migration and accumulation process with contemporaneous structural deformation according to claim 1, wherein the structural deformation control device comprises a lifting device (8), a lifting slider (10) and a translation slider (13); the lifting device (8) is hydraulically driven, and the lifting slider (10) and the translation slider (13) drive the triangular push plate (11) to extend and compress an experimental model in vertical and horizontal directions.

4. The experimental apparatus for physical modeling of a fluid migration and accumulation process with contemporaneous structural deformation according to claim 1, wherein the structural deformation experiment box comprises a frame (16), a base plate (18) and a model support base plate (19); and a transparent window (15) is arranged on the frame (16).

5. An experimental method using the experimental apparatus for physical modeling of a fluid migration and accumulation process with contemporaneous structural deformation according to claim 1, comprising the following steps:

(a) spreading experimental materials (17) in the structural deformation experiment box, and filling the injection pipe (29) with fluids or plastic materials;

(b) placing a structural deformation experiment box in one basket experiment module (21); placing a counterweight with the same weight as the structural deformation experiment box in the other basket experiment module (21), and sealing relevant pipelines;

(c) turning on the centrifuge to allow the running acceleration to reach a set value; and setting the flow rate, flow and pressure of the fluids or the plastic materials on the console (1); and (d) stopping relevant equipment, disconnecting the pipelines and taking out the structural deformation experiment box.

6. The experimental method using the experimental apparatus for physical modeling of a fluid migration and accumulation process with contemporaneous structural deformation according to claim 5, wherein the step of filling the injection pipe (29) with fluids or plastic materials in the step (a) specifically comprises: injecting the fluids or the plastic materials into the fluid cylinders (27) through a feeding port (30) until fluids or plastic materials overflow from an air vent on the fluid cylinders (27); controlling the fluid injection lifting device (25) to descend slowly through the console (1) until fluids or plastic materials overflow from the injection port (24).

7. The experimental method using the experimental apparatus for physical modeling of a fluid migration and accumulation process with contemporaneous structural deformation according to claim 6, wherein in the step (c), the plastic materials are injected when the set injection rate is positive, and the plastic materials are suctioned when the injection rate is negative.

\* \* \* \* \*